United States Patent [19]

Lin

[11] Patent Number: 5,591,896
[45] Date of Patent: Jan. 7, 1997

[54] SOLID-STATE GAS SENSORS

[76] Inventor: Gang Lin, 301 E. Reynolds Dr. 4-C, Ruston, La. 71270

[21] Appl. No.: 552,219

[22] Filed: Nov. 2, 1995

[51] Int. Cl.⁶ .......................... G01N 27/62; G01N 27/52; G01T 1/18
[52] U.S. Cl. ...................... 73/31.05; 73/29.01; 324/453; 324/459
[58] Field of Search ................. 73/31.05, 31.02, 73/31.06, 29.01; 324/455, 453, 459, 464

[56] References Cited

U.S. PATENT DOCUMENTS

| | | | |
|---|---|---|---|
| 3,342,712 | 9/1967 | O'Keefe, Sr. ............... | 204/148 |
| 3,450,620 | 6/1969 | Brewer ....................... | 204/195 |
| 3,649,834 | 3/1972 | Randolph .................... | 250/83.6 FT |
| 3,820,015 | 6/1974 | Jeunehomme ................. | 324/33 |
| 3,926,560 | 12/1975 | Gentry ...................... | 23/254 E |
| 3,999,122 | 12/1976 | Winstel et al. ............. | 324/71 SN |
| 4,025,412 | 5/1977 | La Conti .................... | 204/195 R |
| 4,050,995 | 9/1977 | Bredeweg .................... | 204/1 T |
| 4,169,369 | 10/1979 | Chang ........................ | 73/23 |
| 4,171,341 | 10/1979 | Morgan ....................... | 422/98 |
| 4,227,984 | 10/1980 | Dempsey et al. ............. | 204/195 S |
| 4,394,239 | 7/1983 | Kitzelmann et al. .......... | 204/414 |
| 4,522,690 | 6/1985 | Venkatasetty et al. ........ | 204/1 T |
| 4,542,640 | 9/1985 | Clifford .................... | 73/23 |
| 4,609,875 | 9/1986 | Jeffers ..................... | 324/455 |
| 4,674,320 | 6/1987 | Hirschfeld .................. | 73/23 |
| 4,706,493 | 11/1987 | Chang et al. ................ | 73/23 |
| 4,896,143 | 1/1990 | Dolnick et al. .............. | 340/634 |
| 4,902,391 | 2/1990 | Ibbott ....................... | 204/150 |
| 4,903,099 | 2/1990 | Sekiguchi et al. ........... | 357/25 |
| 4,911,892 | 3/1990 | Grace et al. ................ | 422/94 |
| 5,106,468 | 4/1992 | Chimenti ..................... | 204/180.1 |
| 5,143,696 | 9/1992 | Haas et al. ................. | 422/90 |
| 5,173,166 | 12/1992 | Tomantschger et al. ........ | 204/412 |
| 5,184,500 | 2/1993 | Krema et al. ................ | 73/23.2 |
| 5,191,784 | 3/1993 | Jelley et al. ............... | 73/31.06 |
| 5,281,915 | 1/1994 | Takahama et al. ............ | 324/464 |
| 5,296,196 | 3/1994 | Takeshima ................... | 422/98 |
| 5,302,274 | 4/1994 | Tomantschger et al. ........ | 204/412 |

OTHER PUBLICATIONS

Chemical Sensing with Solid State Devices, M. Madou and S. Morrison, Academic Press, Jul. 1989, pp. 1–12.
Handbook of Chemistry and Physics, 46th Edition, Jan 1991 Table of C. Hodgman, The Chemical Rubber Co., p. E-61.
Ionization Potentials, Edited by R. Weast, S. Selbyand.

(List continued on next page.)

Primary Examiner—Hezron E. Williams
Assistant Examiner—J. David Wiggins

[57] ABSTRACT

Solid state gas sensors are provided, the use of which permits quantitative measurement of gaseous contaminants or change of composition of a gas or atmosphere being monitored. The gas sensor comprises at least a base, a first electrode, a second electrode. The first electrode has a finely tapered end to strengthen the electric field intensity in the gap between the first and the second electrodes. The sensing is based on ionization potential difference between the molecules of the contaminating gas and of the atmosphere. When a high voltage is applied to the electrodes, it creates a strong electric field between the electrodes, especially a very strong electric field around the tapered end of the first electrode. When the potential is sufficiently high, the gas in the vicinity of the tapered end of the first electrode will be ionized. The ions and electrons generated by the ionization create an electric current flows between the two electrodes and across the gap. The changes of this electric current with gas contamination or changes in the gas composition are used as sensing signals. Unlike other gas sensors, there is no chemical reaction, absorption or adsorption involved in this sensing process. The gas sensors of this invention may be manufactured by lithographic micromachining techniques at very low cost, and they can be easily integrated with controller and signal processing circuits to upgrade to smart microsensors. Further, in an alternative embodiment, a micro-actuator to control the gap between the two electrodes is integrated with the sensors. In another alternative embodiment, a third electrode may be mounted so as to control the intensity of the electric field.

20 Claims, 11 Drawing Sheets

A micromachined gas sensor with integrated gap spacing actuator

OTHER PUBLICATIONS

Thin Film Technologies Spur Revolution in Sensing, R & D Magazine, Jun. 1995, pp. 22–26, Tim Studt.

Silicon as a Mechanical Material, Proceedings of the IEEE, vol. 70, No. 5, May 1982, K. Petersen, pp. 420–457.

Departure from Paschen's Law of Breakdown of Gases, W. Boyle and P. Kisliuk, Physical Review Journal, Jan. vol. 97, No. 2, 1955, pp. 255–259.

Micromachines Made of Silicon, J. Bryzek, K. Petersen and W. McCulley, Spectrum, IEEE Journal, May 1994, pp. 20–31.

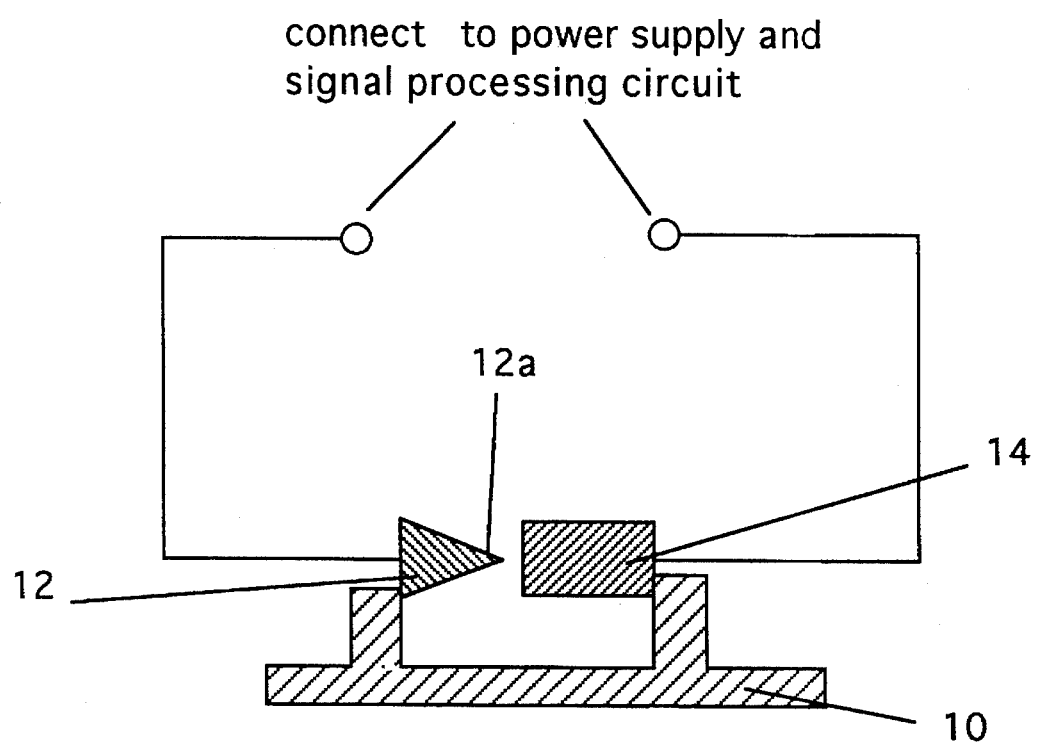
FIG. 1 A schematic cross-section of a gas sensor

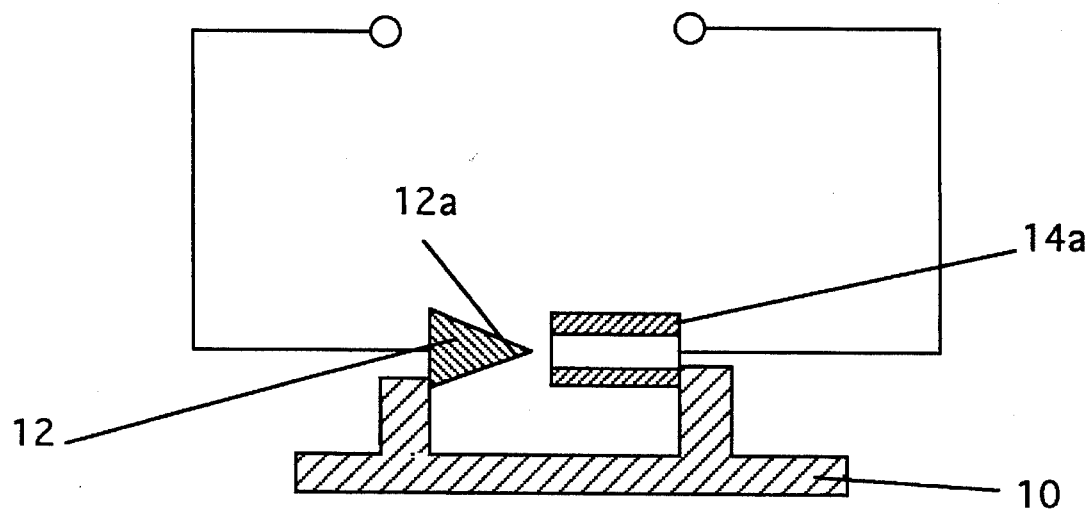
FIG. 2 A mechanically constructed gas sensor

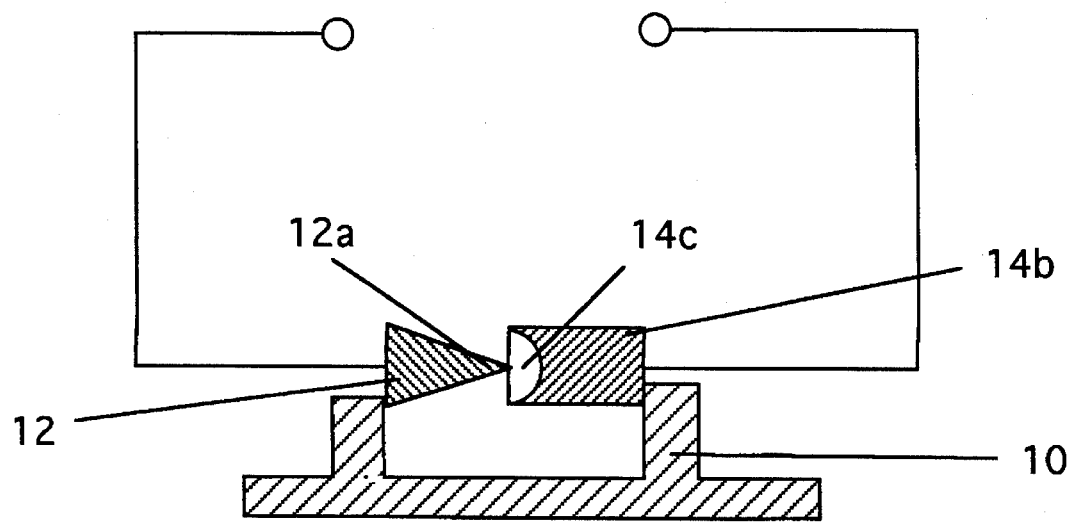
FIG. 3 A mechanically constructed gas sensor

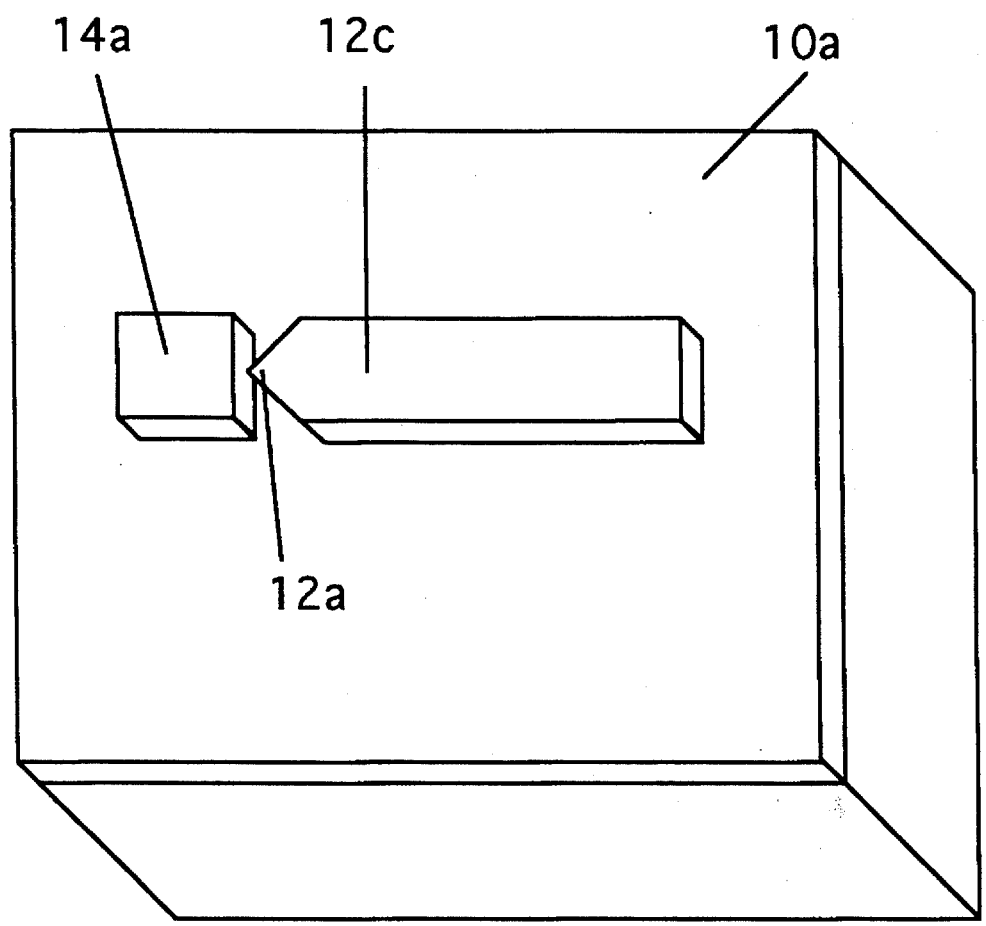
FIG. 4 A micromachined gas sensor

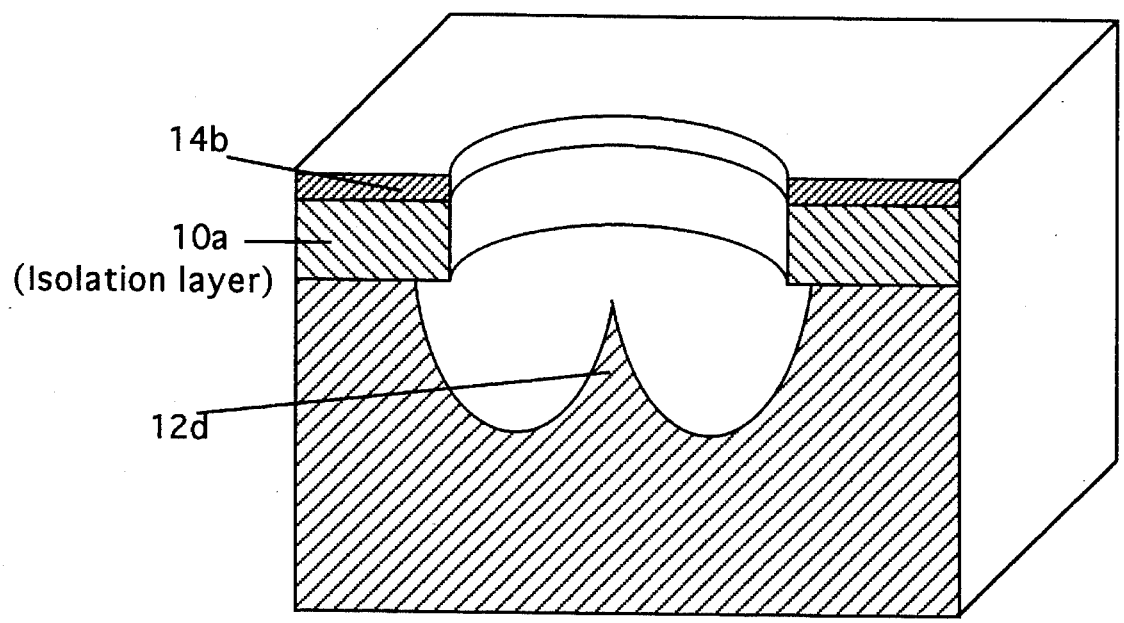
FIG. 5 A cross-section view of micromachined gas sensor

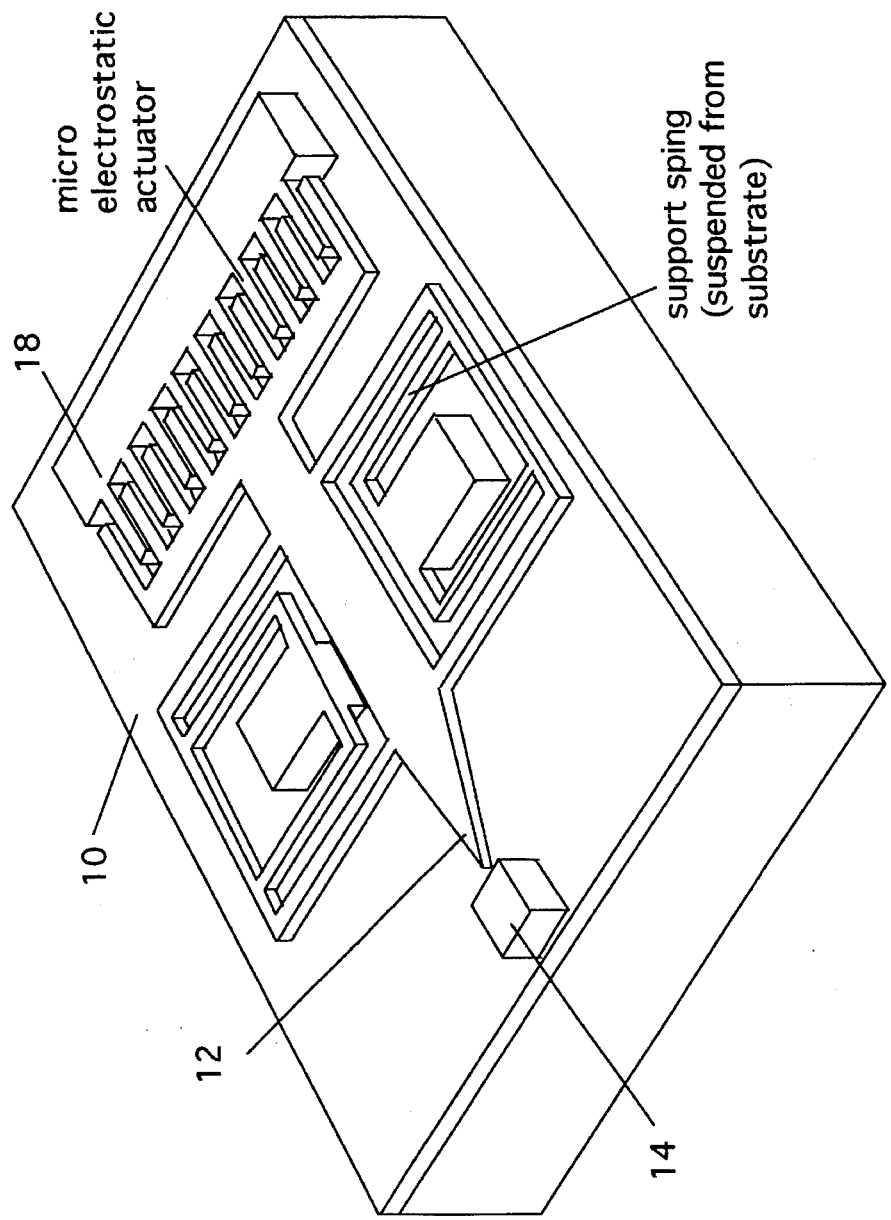
Fig. 6 A micromachined gas sensor with integrated gap spacing actuator

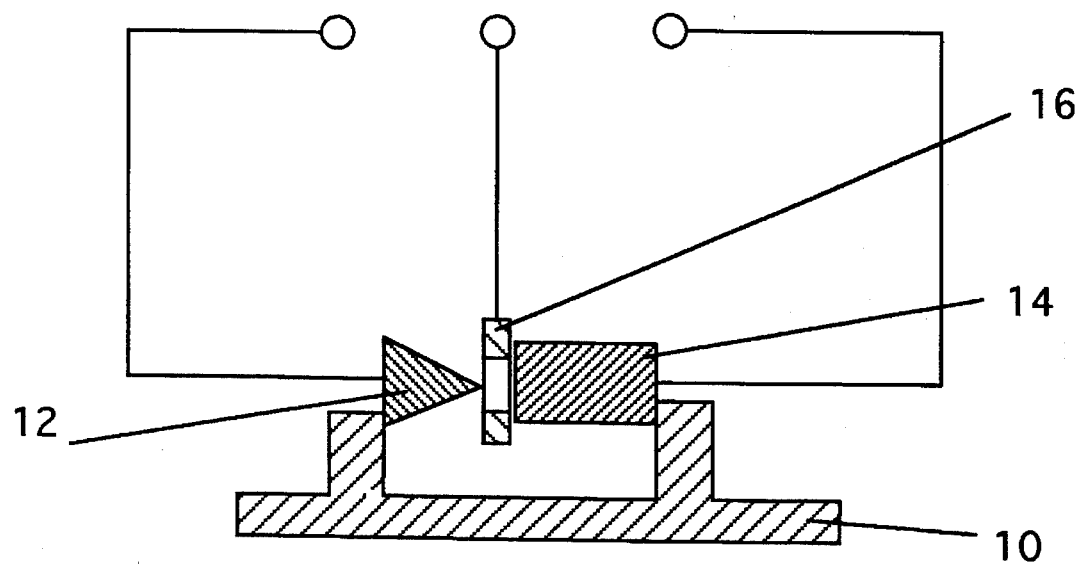
FIG. 7 A gas sensor with three electrodes

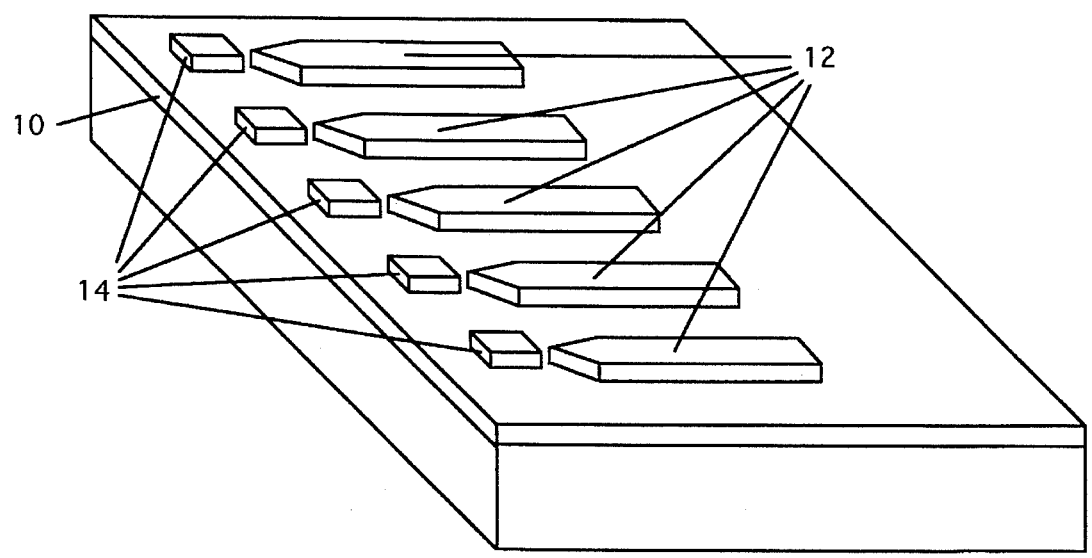
FIG. 8 An array of micro-fabricated solid state gas sensors

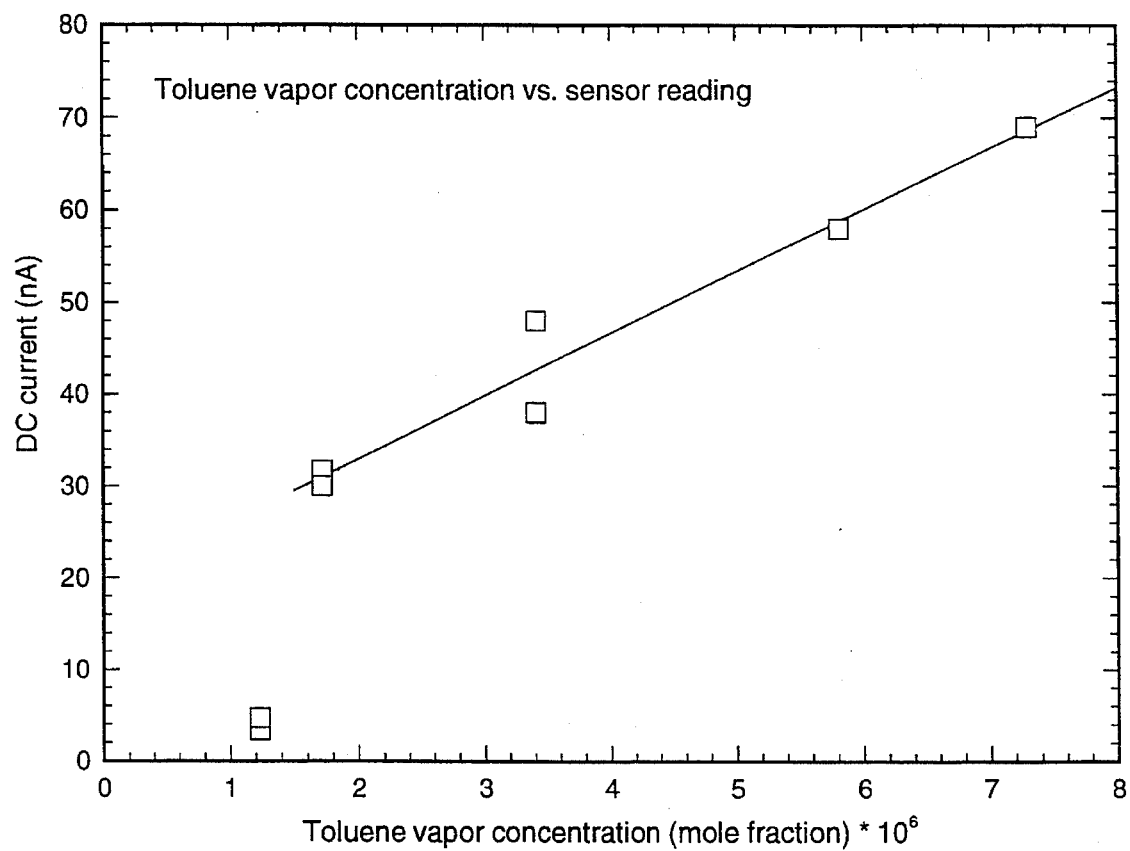
Fig. 9 A typical gas concentration versus detection signal curve obtained with a two electrodes gas sensor

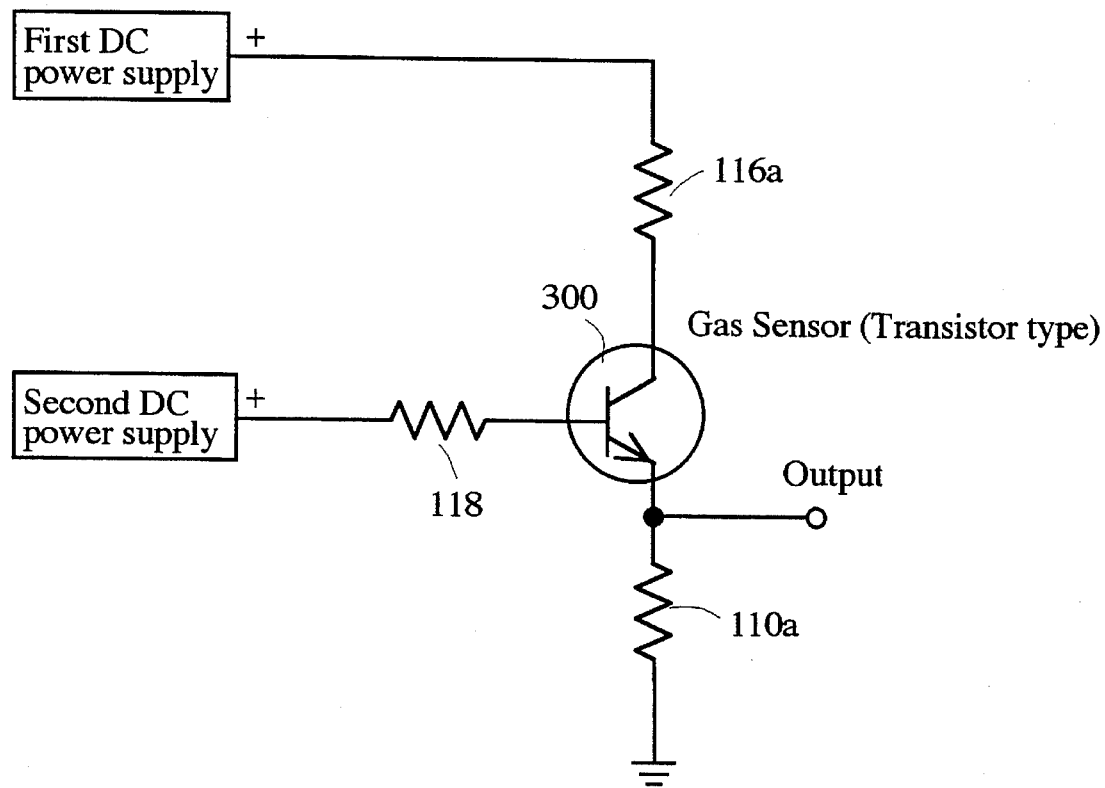
Fig.11 An exemplary circuit used in gas sensor test

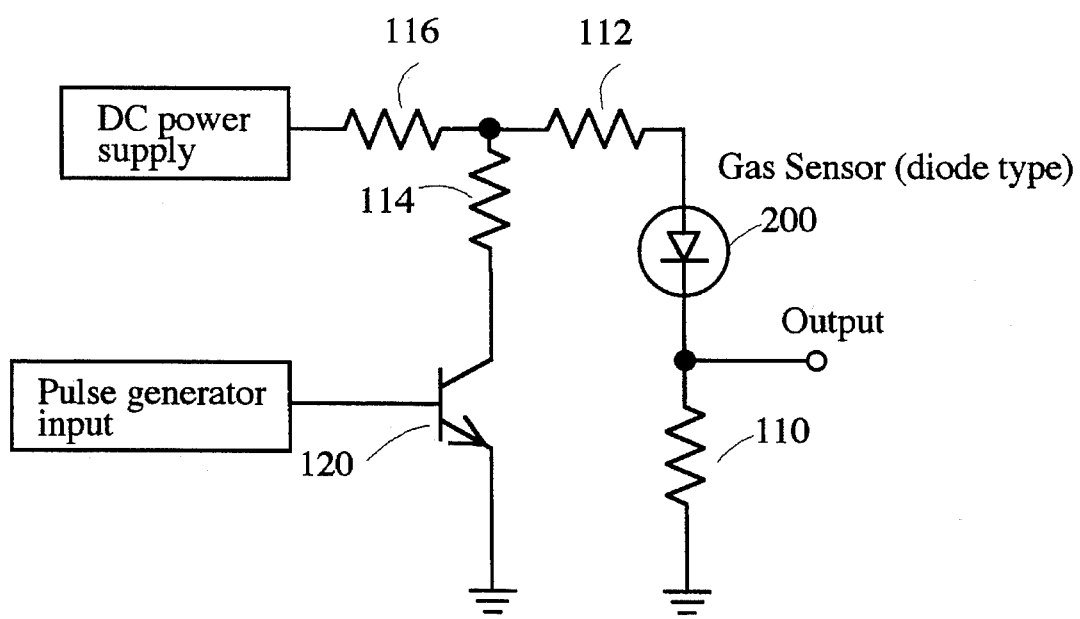
Fig.10 An exemplary circuit used in gas sensor test

SOLID-STATE GAS SENSORS

FIELD OF THE INVENTION

This invention relates to solid-state gas sensors. More particularly, to solid-state gas sensors of a type suitable for monitoring gas contamination or changes in concentration or composition of gas species in a given environment.

BACKGROUND OF THE INVENTION

Most solid-state gas sensors available to date are based on the electrical response of the solid to its chemical environment. That is, the electrical properties of the solids are affected by the presence of a gas-phase species, and this change is employed to detect the species. These solid-state sensors can be divided into three classes: semiconductor sensors where the species to be detected is adsorbed or absorbed and changes the electronic conductivity of the semiconductor; solid electrolyte sensors for use in gas, where the species to be detected affects the Nernst potential or changes the ionic current through the solid; and field-effect-transistor gas sensors (ChemFET), in which the species to be detected affects the potential at the gate of a field-effect transistor.

The semiconductor sensors based on pressed powders and thin films are commercially available. The sensors are designed based on a reaction between the semiconductor and the gases in the atmosphere, which produces a change in semiconductor conductance. One possible reaction is that in which the semiconductor is converted to another compound, or at least to another stoichiometry. For example, one can have a semiconducting oxide which is oxidized by oxygen from the atmosphere, but lattice oxygen is extracted when some organic vapors are introduced into the atmosphere. Thus the presence of the organic vapor lowers the cation/oxygen ratio in the oxide—that is, it changes the stoichiometry of the solid. Such a stoichiometry change (indeed, any change in the composition of the solid) can have a significant effect on the conductivity of the material.

More commonly, with semiconductor gas sensors the "reaction" leading to conductivity changes is considered to be the adsorption of gases. The effects of the gaseous ambient are interpreted to be due not to changes in bulk composition but to adsorption gases on the surface of the semiconducting solid. In the adsorption mechanism, the usual model is as follows: Oxygen from the atmosphere adsorbs and extracts electrons from the semiconductor. If the solid conducts by electrons, the conductivity will decrease as the electrons are extracted. When an organic vapor is present in the atmosphere, it reacts with the negatively charged oxygen, becoming oxidized, perhaps to $H_2O$ and $CO_2$, and the electrons are returned to the solid, restoring the conductivity. Consequently, the conductivity is much higher with the organic vapor present in air than it is for pure air. Of course, sometimes it is difficult to tell which process—stoichiometry changes or adsorption—affects the conductivity change. In most cases, however, the change is sufficiently rapid compared to the expected diffusion rate of the oxygen vacancies (or other species which diffuse) in the solid, so that one can be reasonably certain that the conductivity changes can not be due to changes in bulk composition.

The third possible reaction between the semiconductor and the gas is ion exchange near the surface, a process intermediate between the other two. For example, a surface ion might replace an oxide ion at the surface of the metal oxide semiconductor in the presence of $H_2S$ vapor in the atmosphere. Since sulfides often are much more conductive than oxides, such an exchange may lead to a high surface conductivity.

In solid electrolytes the conductivity stem from mobile ions rather than electrons. Typically the conductivity is dominated by one type of ion only. Solid electrolytes already play an important role in commercial gas and ion sensors. In these applications solid electrolytes are used as nonporous membranes separating two compartments containing chemical species at different concentrations on either side thereof. By measuring the potential across such a membrane, one can determine the concentration of the chemical species on one side if the concentration on the other side (i.e., the reference side) is known. In general the solid electrolytes allow the quantitative determination of the concentration of those species that are ionically transferred in the electrolyte.

The ChemFET is a class of sensors developed recently as variations on field-effect transistors (FETs). In a FET one has a thin channel of conductance at the surface of the silicon, which is controlled by voltage applied to a metal film (a gate) separated from the channel of conductance by a thin insulator layer (e.g., silicon dioxide) It has been found that if the metal film was removed from the FET and either adsorbed gases or ions from the ambient atmosphere appeared at the surface of the gate dielectric, the effect was similar to applying a voltage at the gate. Selectivity can be induced in these sensors by appropriate incorporation of, for example, certain pH-sensitive insulators and ion-sensitive membranes in ion-sensitive field-effect transistors (ISFETs).

Based on the above principles, various solid-state gas sensors have been invented, and their descriptions are available in the patent and other technical literature. For example, U.S. Pat. No. 4,903,099 describes a ChemFET type gas sensor; U.S. Pat. Nos. 4,896,143, 4,706,493, 4,169,369 and 5,143,696 disclose semiconductor-type gas sensors; U.S. Pat. Nos. 4,025,412, 4,227,984, 4,394,239, 4,522,690, 5,302,274, and 5,173,166 disclose electrolytes-type gas sensors; and U.S. Pat. Nos. 5,191,784, 3,450,620 and 5,184,500 disclose some other type of gas sensing devices. Most of these solid-state gas detectors, however, have one or more disadvantages associated therewith, including: (a) sophisticated structure and relatively large size, (b) limited range of detectable gases, (c) limited range of operatable temperature, (d) elevated operation temperature, (e) low sensitivity, (f) slow response, with hysteresis, (g) expensive manufacturing cost, (h) low reliability, (i) installation and operation inconvenience, and (j) low integratability with signal processing integrated circuit (IC).

Accordingly, there exists a need in many industries for enhanced solid-state gas sensors, having the following characteristics: (a) simple structure and small dimension, (b) wide operating range of detectable gas, (c) wide operation range of temperature, (d) atmospheric temperature operability, (e) high sensitivity, (f) rapid response without hysteresis, (g) low manufacturing cost, (h) high reliability, (i) installation and operation convenience, and (j) integratability with signal processing IC.

SUMMARY OF THE INVENTION

In general, the present invention provides a solid-state gas sensor for detecting a contaminant or a change in gas composition in a given atmosphere. The sensor comprises, at least, (a) a base made of a dielectric material; (b) a first electrode with a finely tapered end mounted on said base; (c)

a second electrode mounted on said base near to and spaced apart from said first electrode, thereby forming a narrow gap between said first and second electrodes. By impressing thereon a difference in electrical potential between said first and second electrodes, a strong electric field is formed between said electrodes, and gas molecules to be detected are ionized within said gap. When contamination or change of said gas composition occurs, electric measurement means connected to said first and second electrodes detect said contamination or said change of gas composition by measuring an electric current indicative of said contamination or said change of gas composition.

BRIEF DESCRIPTION OF THE DRAWINGS

FIG. 1 is a schematic cross-section of a first embodiment of a solid state gas sensor, made in accordance with the principles of the present invention.

FIG. 2 is a schematic cross-section of a second embodiment of a solid state gas sensor, made in accordance with the principles of the present invention.

FIG. 3 is a schematic cross-section of a third embodiment of a solid state gas sensor, made in accordance with the principles of the present invention.

FIG. 4 is a schematic representation of a fourth embodiment of a solid state gas sensor, made in accordance with the principles of the present invention.

FIG. 5 is a schematic cross-sectional representation of a fifth embodiment of a solid state gas sensor, made in accordance with the principles of the present invention.

FIG. 6 is a schematic representation of a sixth embodiment of a solid state gas sensor, made in accordance with the principles of the present invention.

FIG. 7 is a schematic cross-section of a seventh embodiment of a solid state gas sensor, made in accordance with the principles of the present invention.

FIG. 8 is a schematic representation of an array of the solid state gas sensors, made in accordance with the principles of the present invention.

FIG. 9 is a graphical representation of a typical curve of sensor output versus concentration of a gaseous species, using a solid-state gas sensor made in accordance with the principle of the present invention.

FIG. 10 is an exemplary electric circuit used in testing a solid state gas sensor, made in accordance with the principles of the present invention.

FIG. 11 is an exemplary electric circuit used in testing a solid state gas sensor, made in accordance with the principles of the present invention.

REFERENCE NUMERALS IN DRAWINGS

10 base
12 first electrode
14 second electrode
16 third electrode
18 micro comb-type electrostatic actuator
110 electric resistor
112 electric resistor
114 electric resistor
116 electric resistor
118 electric resistor
120 transistor used as an electric switch

200 gas sensor of diode type under testing
300 gas sensor of transistor under testing

DETAILED DESCRIPTION OF THE PRINCIPLE OF THE INVENTION

While I believe the following discussions on theory underlying my present invention is correct, I don't wish to be bound by said theory.

The present invention provides a type of solid state gas sensors based on an entirely different principle from all the solid-state gas sensors of the prior art. As described above, in the section entitled "BACKGROUND OF THE INVENTION", most gas sensors are build to respond to on one or more of the following phenomena: chemical reaction, absorption, or adsorption. The sensors of the present invention, however, are built to respond to molecule ionization phenomenon. More specifically, difference of ionization potential due to inherent molecular structural difference in various gaseous species is detected by the sensor. The simplest structure comprises first and second electrodes facing to each other across a narrow gap. The first electrode tapers to an apex. The second one could be of any of many different shapes, such as a solid cylinder or a cylindrical tube. The optimal shape for the second electrode is one which will maximize electric field intensity in a small hemisphere with the apex of the first electrode disposed in the center thereof. A summary of the basic sensor operating principle follows.

When a high voltage is applied to the two electrodes across the gap, it creates a strong electric field around the apex of the needle. When the potential is sufficiently high, the gas in the vicinity of the apex will be ionized. The ions and electrons generated by the ionization create an electric current flowing between the two electrodes across the gap. The changes of this electric current with gas composition are used as sensing signals.

The theory underlying the electrical breakdown of gas molecules within an atmospheric pressure gap is relatively well known, and the electric potential required to cause such breakdown is often called Paschen minimum for atmospheric pressure discharge, which is about 340 V for air. In the present invention, the needle apex is used as a mechanism to enhance the electric field to lower the required operating voltage (possibly below the Paschen minimum) and to increase the sensitivity. Polarity can set with the needle as either cathode or anode. The needle cathode design usually has a higher sensitivity than that of the needle anode design. The theory underlying the ionization mechanism in the needle cathode design is as follows: a random ionization event in the gap triggers the breakdown by supplying the positive ion needed to enhance the field emission. The field emitted electrons then cause an avalanche in the gap, with electron impact ionization and electron attachment to form gaseous positive and negative ions. The conduction mechanism seems to be a microscopic glow discharge supported mainly by the latter charged species. The theory underlying the ionization mechanism in the needle anode design is, however, not well known yet. In practical sensor design, a current limiting resistor should be used to prevent the development of an atmospheric pressure arc. Although the discharge seems like a steady, direct current (DC) glow, it is actually a sequence of non-sustaining discharge pulses. The current-voltage relationship for the discharge pulses is a function of the electrode separation (gap), the radius of curvature of the needle and the composition of the gas.

The basic mode of operation employs two electrodes like a diode device which conducts electricity across a gap filled with gas at atmospheric pressure, and the small contamination of impurities may significantly affect the conductivity. The atmosphere in the diode device or sensor, could, e.g., include ambient air (with humidity), pure dry air, dry nitrogen, argon, oxygen, or carbon dioxide. Detectable impurities include, e.g., alcohols, ketones, water vapor, aromatic hydrocarbons and chlorocarbons.

The sensor utilizes either a DC mode or a pulsed mode. The DC mode of operation simply records the averaged DC current flowing between electrodes. A net DC current measured with a high impedance in the circuit is really a series of breakdown pulses recorded as a quasi-steady current. A high circuit impedance should be used in order to avoid the development of a current avalanche. The pulse mode of operation is preferable for practical reasons, in order to keep needle apex erosion to a minimum and to facilitate pulse-counting detection rather than DC current measurement.

In addition to the basic diode structure, the sensor can be modified by adding more electrodes to the simple two electrodes structure. If we see the two electrodes in the diode system as anode and cathode in a vacuum tube, then the third electrode can be seen as a grid in the vacuum tube. The third electrode adds a controllability of the electric current flowing through anode to cathode. This modification adds special features for some applications to the sensors, but also makes the sensors more sophisticated and more expensive to manufacture.

The sensitivity to a gas specie to be detected from a specific atmosphere depends largely on (a) difference in the ionization potentials between the background atmosphere and the gas to be detected, (b) the operating voltage of the sensor, (c) the clearance of the gap, and (d) the radius of curvature (sharpness) of the needle apex. In general, the sensitivity of the sensors is, compared with state-of the art sensors, very high.

It should be noted that the gap of interelectrode spacing in the sensors must be larger than the mean free path of the gas molecules, and that the voltage of the power supply for the sensor must be higher than the ionization minimum required to cause electrical breakdown of the gas.

The present invention provides solid-state gas sensors based on principles of molecule ionization, which differs with all prior-art sensors. The gas sensors provided by the present invention are able to detect small changes in the composition of gases in air or other environments. These sensors have the following advantages: (a) they have very simple structure so they are very small in size; (b) they operate at almost any temperature and do not require temperature control, nor do they require heaters to reach an elevated operating temperature; (c) they works in a wide range of impurity concentration; (d) they have a real time response and little hysteresis (e) they have very high sensitivity; (f) their structure are suitable for micro-machining techniques commonly used in the semiconductor industry, so that they are very inexpensive to manufacture.

The above and other effects, features and advantages of the present invention will be apparent to those skilled in the art from the following detailed description of various embodiments thereof, in conjunction with the accompanying drawings.

DESCRIPTION OF PREFERRED EMBODIMENTS

The basic structure of a gas sensor made in accordance with the principle of the present invention comprises a first electrode 12 and a second electrode 14 mounted on a base 10 in such a manner that the first and second electrodes face each other across a small gap filled with atmosphere gas. In addition to this basic structure, a linear actuator 18 to control the gap clearance, and a third electrode 16 to control the intensity of the electric field within the gap, may optionally be added to the sensor to improve its performance.

More specifically, reference is made to FIG. 1, in which is shown a first embodiment of a solid-state gas sensor made in accordance with the principle of the present invention, and generally designated by the numeral 1. The base 10 of the sensor 1 is made of non-conductive solid material. The first electrode 12 is a fine cylindrical needle tapered to an apex 12a by chemical or electrochemical means. The second electrode 14 is a solid cylinder with a flat cut at its end perpendicular to its axis. The electrodes 12 and 14 are preferably made of high-strength material such as tungsten.

FIG. 2 shows a second embodiment 2 of a solid-state gas sensor made in accordance with the principles of the present invention. The finely-tapered cylindrical needle 12 which function as the first electrode fits into a coaxial cylinder 14a which serves as the second electrode. The advantage of this arrangement is a constant gap, which approximately equals the inner radius of the cylinder, between two electrodes.

Reference is now made to FIG. 3, in which is shown a third embodiment of a solid-state gas sensor made in accordance with the principles of the present invention and generally designated by the numeral 3. The structure of the sensor 3 optimizes the second electrode 14b by fabricating a hemisphere 14c at its face with the needle apex 12a of the first electrode 12 in its center, to maximize the electric field intensity within the gap. The advantage of this embodiment is to minimize the operating voltage and to provide the highest sensitivity of the sensor 3.

Both second and third sensors 2 and 3 are preferably made of same material as those of the first embodiment 1 shown in FIG. 1.

FIG. 4 shows a fourth embodiment 4, which is preferred because of its low manufacturing cost by mass-production using non-assembly micro-fabrication techniques commonly used in the semi-conductor industry. The first and second electrodes 12c and 14a are made of a thin conductive coat deposited upon a nonconductive substrate, and the material for the electrodes 12c and 14a can be any thing provided it is conductive and strong. This particular embodiment 4 is especially suitable for lithographic surface micromachining and its advantages include being very inexpensive to manufacture, and having good uniformity between sensors so made in terms of the needle sharpness of the apex 12a of the first electrode 12c, and in the clearance of the gap.

FIG. 5 shows a fifth embodiment 5 constructed and arranged to take advantage of bulk micro-fabrication techniques. The pyramidal first electrode 12d is formed by anisotropic etching with a simple circular symmetry (annular pattern) mask, and can be made directly from highly doped silicon substrate. The second electrode 14b is a conductive layer deposited above an isolation layer 10a which is an equivalent of the base 10 in FIGS. 1 to 4. The dimensions of the annular pattern can be varied over a range, but the electrode gap should be no less than the mean free path of molecules of the gas to be detected. In comparison with the surface micro-machined embodiment 4 shown in FIG. 4, this bulk micromachined embodiment 5 may offer a better enhanced electric field around its needle apex 12a, but it is more difficult and costs more to manufacturing.

It should be noted that, although field emitters used for flat panel displays have a similar structure to the embodiment 5 shown in FIG. 5, they are very different in design principles. The emitter is designed to operate in vacuum, with negatively connected first electrode as electron emitting gun, while the sensor is designed to work in gaseous atmosphere and it is operatable with first electrode as either anode or cathode. Further more, the emitter designed to operate in vacuum has much smaller emitter gap and much lower operating voltage, typically the gap is less than one micron and the operating voltage is about three volts. In comparison, the sensor designed in accordance with the principles of the present invention has a gap of several to few tens of micron and operating voltage of about three hundred volts. In other words, the gap of the sensor must be greater than the mean free path of molecules of the gas, and the operating potential must be greater than the Paschen minimum for atmospheric pressure discharge.

FIG. 6 shows a sixth embodiment 6 of a sensor made in accordance with the principles of the present invention. The sensor 6 integrates a micro-machined linear electrostatic comb-type actuator 18 to control the gap clearance. A micro comb-type actuator is roughly a few hundred microns×a few hundred microns and is driven by electrostatic force generated by an electric potential difference between the two sides of the combs. When a high voltage is applied on the actuator, the attraction between the two sides will reduce the distance between the teeth by actuating the movable tooth. The moving half of a micro comb-type actuator is suspended above the substrate by several spring-like supports. Microfabrication technique for micro comb-type actuators has been well studied and developed in the last few years. The advantage of this sophisticated embodiment is, besides being relatively easy to fabricate on a silicon substrate, that it enables the user to measure the current response at various gaps, or to keep the electric current through the gap constant while using the voltage or the clearance as outputs. It would appear this embodiment 6 could make more measurements than the first embodiment 1, and is suitable for tasks where more sophisticated measurements are required. The advantage of the sixth embodiment 6 is best taken when it is integrated into a more sophisticated system in which more than one type of sensors and signal processing and controlling integrated circuits (ICs) are combined. The sensor 6 is, however, more expensive to manufacture, and should be used only where its sophistication is necessary.

In addition to the basic two electrode diode-like structure shown in FIGS. 1–6, the sensor can be naturally extended to a transistor-like structure by incorporating a third electrode. A seventh embodiment 7 based on this principle is shown in FIG. 7. The first electrode 12 and second electrode 14 in this three electrodes structure 7 can be viewed as the equivalents of anode and cathode in a vacuum tube, so that the ring-shaped third electrode 16 can be thought of as similar to a grid in a vacuum tube. The third electrode 16 controls the electric current through the anode (12 or 14) to the cathode (14 or 12). Although not shown in drawings, the third electrode 16 can easily be added to the embodiments 1–6 shown in FIGS. 1 through 6. The third electrode modification 7 adds special features to the sensors for some applications such as atmosphere change compensation through the third electrode 16, but it also makes the sensors more sophisticated and more expensive to manufacturing. Like the sensor 6 shown in FIG. 6, the advantage of this embodiment is best taken when it is integrated into a more sophisticated system in which more than one type of sensors, as well as signal processing and controlling ICs, are combined, and it should be used only where the added sophistication is really needed.

For an industrial application, the sensors 1–7 may be produced in an array or a matrix on a substrate to form a sensing device as shown in FIG. 8. The detector device with multiple sensors may have better accuracy, redundancy and reliability than that of a single sensor. A typical unpackaged detector chip, which may include dozens of sensors in an array or a matrix, fabricated according to the above procedure may have dimensions as small as 1.0 mm×1.0 mm×0.5 mm, or it may be larger or smaller. Since these sensors 1–7 are batch fabricated on a silicon wafer, they can be mass-produced very inexpensively.

Reference is now made to FIG. 9, wherein is shown a typical curve for a two-electrode gas sensor made in accordance with the principle of the present invention. The drawing shows ammetric response to various concentrations of toluene in the gas being monitored (dry nitrogen). The data were taken at room temperature (approximately 25° C.) with nitrogen as the background atmospheric gas. The particular sensor used to take these data has a negative polarity and an electrode gap of twenty-five microns which is formed between a one micron radius apex and an opposite electrode having an inner curvature of 50 microns. The sensor operates at five-hundred volts DC and the response is sufficiently rapid to be considered as real-time. Similar curves were obtained with ethanol, acetone and water vapor as the impurity.

Two simple circuits used for sensors' tests, one for the diode type and the other one for the transistor type, are shown in FIG. 10 and FIG. 11. The resistors 110, 112, 114, 116 and 118 are used to prevent the electric current from over flowing. In FIG. 10, a transistor 120 is used as an electric switch for pulse generator to control the high voltage imposed on the sensor. The sensor output in both circuits is connected to either a multimeter for simple reading or a FFF for further analysis. Ideally the pulse generator and a signal analyzer should be modularized and integrated with the sensor on a single chip.

Among all the sensor embodiments, the embodiments 4 through 8 are more suitable for lithographic micro-machining. Fabrication of these sensors presents no particular difficulty to those who are familiar with lithographic micro-machining techniques. A typical process for the embodiment 4 is only described here as an example of micromachining technology for ease of reference. The process follows: (a) depositing a thin silicon nitride dielectric layer on a silicon substrate (a wafer) using a microfabrication process, for example CVD (chemical vapor deposition); (b) depositing a high quality polysilicon layer above the silicon nitride by LPCVD (low pressure CVD); (c) depositing a PSG (phosphorus-doped silicon dioxide) layer above the polysilicon layer; (d) doping the polysilicon layer through the PSG layer by 1000° C. annealing the wafer for one hour; (e) spin-coating a layer of photoresist above the PSG; (f) patterning (i.e. exposing and developing) electrodes and electric connection pads with a photomask designed according to the embodiment 4; (g) etching the PSG layer with a photoresist mask by RIE (reactive ion etching); (h) etching the polysilicon layer with the PSG mask by RIE (reactive ion etching) (i) sputtering a gold layer on the pads for wire-bonding: (j) wire-bonding and packaging the sensors with appropriate packaging material. Optionally, circuitry module for powering sensor, pulse generation and signal analysis could also be fabricated on the same silicon substrate as the sensors.

Alternatively, conventional method can also be used in fabrication of the sensors if the number of the sensors needed is too small to take advantage of the micromachining technology and sensor structure is not too sophisticated to require micro machining technology.

OPERATION OF PREFERRED EMBODIMENTS

In each of the embodiments 1–6, the first and second electrodes, and in the seventh embodiment 7 the third electrode, are exposed to the atmosphere. Stated in the simplest terms, in the event of a change in gas composition, there will be a change in the electric current flowing through electrodes, and it is this change and the detection of that measurement thereof which are indicative of the change in the composition of the gas, or of the containment of the gas.

Clearly, in order for there to be a sensing of electric current or potential between the electrodes, there must be a conductive means associated therewith, and electrical measurement means must be provided. In general, the conductive wires in embodiments 4–6, are patterned on same layer of material used for electrodes. Alternatively, wire bonding could be used. The electrical measurement means between the electrodes may be such as a ammeter, a pulse counter, a voltmeter, or a combination thereof.

In order to detect the existence of a gas, the voltage applied to electrodes must be sufficiently high to ionize the molecules of the gas. Generally speaking, the higher the voltage of the power supply, the greater the electric-current output signal.

For the embodiments 1–5, the basic mode of operation is that of using two electrodes like a diode device that conducts electricity across a gap filled with a gas at atmospheric pressure, and a small concentration of impurities affects the conductivity. The atmosphere in the diode device or sensor, could, e.g., be ambient (humid) air, pure dry air, dry nitrogen, argon, oxygen and carbon dioxide; and impurities that can be detected include, inter alia, alcohols, ketones, water vapor, aromatic hydrocarbons and chlorocarbons.

The sensors 1–7 function in either a DC mode or a pulsed mode. When the sensor is operated on a DC mode, the readout signal of the electric current is actually a deviation from its before-contamination background level. Since most volatile gases have a lower ionization potential than air, the electric current is usually increased when the atmosphere is contaminated by a volatile gaseous impurity. The increase (or decrease) in electric current is generally proportional to the degree of contamination or to the concentration of the contaminate, thereby permitting quantitative determination of the concentration of the gaseous impurity.

It would appear that the sensors 1–5 of the present invention, operating in the simple diode mode, are most suitable for applications wherein the atmosphere is well controlled and the contamination source or possible change of composition is predictable, such as the monitoring of a manufacturing processing, or the monitoring of other standard environments.

Since a net DC current measured with a high impedance in the circuit is really a series of breakdown pulses recorded as a quasi-steady current, a spectrum of time history of the current response to a pulse input, which is often called a signature of the gas, can be obtained by signal-processing means. The species of contamination may therefore be determined by spectral analysis, such as comparing its spectrum with spectra of known gases.

The sixth and seventh embodiment 6 and 7 are suitable for more complicated situations wherein the atmosphere is not well controlled and the contamination is not predictable. One suggested method for determining a contaminant is to create response maps of several possible contaminates with respect to a few controllable sensor variables such as gap clearance, potential on the third electrode, etc. By comparing the responses with those of a known gas, the contaminates may be identified. Further, other types of sensor and more sophisticated analysis methods can also be combined therewith to identify the contaminate in complicated applications.

In conclusion, the present invention provides a solid-state gas sensors for contaminant detection or gas composition monitoring which has the following desirable characteristics: (a) simple structure and very small size, (b) wide operation range of temperature, (c) wide operating range of detectable gas, (d) operation at ambient temperature (no heating required), (e) high sensitivity for certain applications, (f) rapid (millisecond) response time with little or no hysteresis, (g) low manufacturing cost through silicon-based micro-fabrication, (h) high reliability, (i) installation and operation convenience, (j) easy integration with signal processing IC on a single chip through a compatible fabrication method.

While certain specific embodiments and details have been described in order to illustrate the present invention, it will be apparent to those skilled in the art that many modifications can be made therein without departing from the spirit and scope of the invention. For example, the sensors can have multiple sensing unit, or can be used to integrate a more sophisticated artificial intelligence controller, with three electrodes and an actuator, e.g., all fabricated on one signal chip, or the substrate used for fabricating the base can be glass rather than a silicon wafer. The scope of the present invention, then, is to be determined by the appended claims in the light of the specification and of the doctrine of equivalents, rather than by the specific examples and details hereinabove.

What is claimed is:

1. A solid-state gas sensor for detecting a gaseous contaminant, a gaseous compound or a change of composition of a gas in a given atmosphere, comprising:

a) a dielectric surfaced base substrate;

b) a first electrode mounted on said base;

c) a second electrode mounted on said base, said second electrode being disposed near and spaced apart from said first electrode, thereby forming a gap between said first and second electrodes, thereby establishing a baseline electric current response for said sensor in the presence of negligible gaseous contaminants or an unchanging gas composition;

wherein, a difference of electrical potential is impressed on said first and second electrodes to ionize gas molecules within said gap between said first and second electrodes;

wherein each of said first and second electrodes is connected to electrical measurement means for the purpose of signal analysis and signal processing;

whereby, when a contamination or changes in said gas composition occur in the area surrounding said gap, said electrical measurement means detect the change caused by a corresponding change in ionization characteristics at said gap in form of electric current response, which amplitude and time dependent behavior of said change in electric current response form thereby is indicative of the contamination or the changes in said gas composition.

2. The solid-state gas sensor of claim 1, wherein said first electrode tapers to an apex, thereby enhancing the electric field between said electrodes.

3. The solid-state gas sensor of claim 1, wherein said gap between said first and second electrodes is greater than the mean free path of molecules of said gas, whereby constant gas flow through said gap provides constant detection.

4. The solid-state gas sensor of claim 1, wherein said first and second electrodes provides a electric field intensity greater than the ionization potential of molecules of said gas, whereby electrons and ions produced by said gas between said first and second electrodes generate said electrical current to effect detection of said contamination or said change of said composition of said gas through resultant modulations, deviations, steady state shift or transient signals superimposed upon said electrical current.

5. The solid-state gas sensor of claim 1, where said potential difference is a direct-current (DC) potential difference.

6. The solid-state gas sensor of claim 5, where said electric measurement means for said electric current response comprises an ammeter connected in an electrical circuit across said first and second electrodes.

7. The solid-state gas sensor of claim 1, where said electric potential is pulsed.

8. The solid-state gas sensor of claim 7, where said electric measurement means include a pulse counter and/or a signal analyzer for the spectrum of time history corresponding to said pulse.

9. The solid-state gas sensor of claim 1, wherein said first and second electrodes are fabricated by lithographic micro-machining techniques.

10. The solid-state gas sensor of claim 9, further comprising:
   d) an integrated circuit designed to perform said electric measurement and signal processing.

11. The solid-state gas sensor of claim 1, wherein said sensor is adapted to develop a specific electric response in the absence of a contaminant gas in said atmosphere being monitored, and said specific electric response changes predictably according to the change expected to occur in said gas composition of said atmosphere.

12. The solid-state gas sensor of claim 1, further comprising:
   d) an actuator to control the dimensional inter-spacing of said gap between said first and second electrodes;
   e) an integrated circuit designed to perform said electric measurement and signal processing.

13. The solid-state gas sensor of claim 12, wherein said actuator and said electrodes are fabricated by lithographic micro-machining techniques.

14. The solid-state gas sensor of claim 1, further comprising:
   d) a third electrode which functions like a grid in a vacuum robe and thereby strengthens or weakens said field provided by said first and second electrodes disposed adjacent to the area of said gap and electrically connected to a controlled and adjustable voltage potential;
   e) an integrated circuit designed to perform said electric measurement and signal processing.

15. The solid-state gas sensor of claim 14, wherein said electrodes are fabricated by lithographic micro-machining techniques.

16. The solid-state gas sensor of claim 1, further comprising:
   d) a number of said gas sensor itself to form an array of sensing units which offers better redundancy, accuracy and reliability of the solid-state gas sensor itself and said change in electric current response for each and all of said number of gas sensor;
   e) an integrated circuit designed to perform said electric measurement and signal processing.

17. The solid-state gas sensor of claim 16, wherein said electrodes of said sensing units are fabricated by lithographic micro-machining techniques.

18. The solid-state gas sensor of claim 1, wherein said dielectric surface of said base substrate is made of dielectric material selected from the group consisting of undoped silicon, siliconnitride and silicondioxide.

19. The solid-state gas sensor of claim 1, wherein said electrodes are made of conductive material selected from the group consisting of doped single crystalline silicon, doped polysilion, metallic surfaced dielectric silicious materials and electroplated metals.

20. The solid-state gas sensor of claim 1 modified to operate as a fluidic substance detector, wherein said contaminant is a fluidic substance instead of gaseous compounds and said atmosphere is formed from a dielectric fluid instead of said gas.

* * * * *